United States Patent
Cosimbescu et al.

(10) Patent No.: US 7,056,601 B2
(45) Date of Patent: Jun. 6, 2006

(54) OLED DEVICE WITH ASYMMETRIC HOST

(75) Inventors: Lelia Cosimbescu, Rochester, NY (US); William B. Vreeland, Webster, NY (US); Scott R. Conley, Rochester, NY (US); Jeri L. Mount, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/692,562

(22) Filed: Oct. 24, 2003

(65) Prior Publication Data

US 2005/0089715 A1   Apr. 28, 2005

(51) Int. Cl.
*H05B 33/14* (2006.01)

(52) U.S. Cl. .............. 428/690; 428/917; 313/504; 313/506

(58) Field of Classification Search .......... 428/690, 428/917; 252/301.16; 313/504, 506
See application file for complete search history.

(56) References Cited

U.S. PATENT DOCUMENTS

| 5,281,489 | A   | * | 1/1994  | Mori et al. ............... 428/690 |
| 6,361,886 | B1  |   | 3/2002  | Shi et al. |
| 6,413,658 | B1  | * | 7/2002  | Araki ...................... 428/690 |
| 6,465,115 | B1  |   | 10/2002 | Shi et al. |
| 6,582,837 | B1  |   | 6/2003  | Toguchi et al. |
| 6,713,192 | B1  | * | 3/2004  | Fukuoka et al. .......... 428/690 |
| 2002/0160296 | A1 | * | 10/2002 | Wolk et al. ............... 430/200 |
| 2003/0087126 | A1 |   | 5/2003  | Ishida et al. |
| 2004/0058193 | A1 | * | 3/2004  | Hatwar ..................... 428/690 |

FOREIGN PATENT DOCUMENTS

| EP | 1 009 044 | 6/2000 |
| EP | 1009044 A2 * | 6/2000 |
| JP | 99323323 | 11/1999 |
| JP | 2000-273056 | 10/2000 |
| JP | 2001-97897 | 4/2001 |
| JP | 2003-261472 | 9/2003 |
| JP | 2003-306454 A * | 10/2003 |
| JP | 2004059535 | 2/2004 |
| WO | WO 2003/087023 A1 * | 10/2003 |
| WO | 2004/018587 | 3/2004 |

OTHER PUBLICATIONS

L. Cosimbescu, et al., Electroluminescent Device with Anthracene Derivative Host, U.S. Appl. No. 10/693,121 (D-86999) filed Oct. 24, 2003.
X. Jiang, et al., "A Blue Organic Emitting Diode From Anthracene Derivative" Thin Solid Films, 401, pp. 251-254.
S. Wen, et al., "Doped RGB Organic Electroluminescent Devices Based on a Bipolar Host Material", Optoelectronics, Proceedings of the Sixth Chinese Symposium, Sep. 12-14, 2003, IEEE, pp. 263-265.

* cited by examiner

*Primary Examiner*—Dawn Garrett
(74) *Attorney, Agent, or Firm*—Arthur E. Kluegel

(57) ABSTRACT

Disclosed is an OLED device comprising an anode and a cathode and located there-between a light emitting layer containing a light emitting dopant and a host comprising a monoanthracene derivative of formula (I):

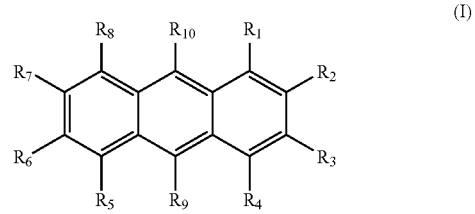

wherein
$R_1$–$R_8$ are H;
$R_9$ is not the same as $R_{10}$;
$R_9$ is a biphenyl group containing no fused rings with aliphatic carbon ring members;
$R_{10}$ is an ortho-substituted- or meta monosubstituted phenyl group;
provided that $R_9$ and $R_{10}$ are free of amines and sulfur compounds.

26 Claims, 1 Drawing Sheet

OLED DEVICE WITH ASYMMETRIC HOST

CROSS-REFERENCE TO RELATED APPLICATION

This application is being co-filed with commonly assigned application entitled "ELECTROLUMINESCENT DEVICE WITH ANTHRACENE DERIVATIVE HOST", Ser. No. 10/693,121, now abandoned in favor of Continuation-in-Part U.S. Ser. No. 10/950,614, filed Sep. 27, 2004.

FIELD OF INVENTION

This invention relates to organic electroluminescent (EL) devices comprising a light-emitting layer containing a host and a dopant where the host comprises a monoanthracene compound with a desirable operational stability at 70° C.

BACKGROUND OF THE INVENTION

While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322–334, 1969; and Dresner U.S. Pat. No. 3,710,167, issued Jan. 9, 1973. The organic layers in these devices, usually composed of a polycyclic aromatic hydrocarbon, were very thick (much greater than 1 μm). Consequently, operating voltages were very high, often >100V.

More recent organic EL devices include an organic EL element consisting of extremely thin layers (e.g. <1.0 μm) between the anode and the cathode. Herein, the term "organic EL element" encompasses the layers between the anode and cathode electrodes. Reducing the thickness lowered the resistance of the organic layer and has enabled devices that operate much lower voltage. In a basic two-layer EL device structure, described first in U.S. Pat. No. 4,356,429, one organic layer of the EL element adjacent to the anode is specifically chosen to transport holes, therefore, it is referred to as the hole-transporting layer, and the other organic layer is specifically chosen to transport electrons, referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by Tang et al [*J. Applied Physics*, Vol. 65, Pages 3610–3616, 1989]. The light-emitting layer commonly consists of a host material doped with a guest material. Still further, there has been proposed in U.S. Pat. No. 4,769,292 a four-layer EL element comprising a hole-injecting layer (HIL), a hole-transporting layer (HTL), a light-emitting layer (LEL) and an electron transport/injection layer (ETL). These structures have resulted in improved device efficiency.

Anthracene based hosts are often used. An useful class of 9,10-di-(2naphthyl)anthracene hosts has been disclosed in U.S. Pat. No. 5,935,721. Bis-anthracene compounds used in the luminescent layer with an improved device half-life have been disclosed in U.S. Pat. No. 6,534,199 and U.S. Pat. No. 0,136,922. Electroluminescent devices with improved luminance using anthracene compound have been disclosed in U.S. Pat. No. 6,582,837. Anthracenes have also been used in the HTL as disclosed in US6465115. In addition there are other disclosures of using anthracene materials in OLED devices, JP2000273056, U.S. Pat. No. 5,972,247, JP2001097897, U.S. Pat. No. 0,048,687, WO 03/060956, WO 02/088274, EP 0429821, WO 03/007658, JP 2000053677, and JP 2001335516.

Despite these advances, there is a continuing need for hosts that have better operational stability and are conveniently manufactured. Improved operational stability of OLED devices will allow their use in more products.

SUMMARY OF THE INVENTION

The invention provides an OLED device comprising an anode and a cathode and located there-between a light emitting layer containing a light emitting dopant and a host comprising a monoanthracene derivative of formula (I):

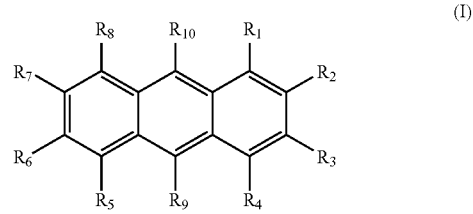

wherein
$R_1$–$R_9$ are H;
$R_9$ is not the same as $R_{10}$;
$R_9$ is a biphenyl group containing no fused rings with aliphatic carbon ring members;
$R_{10}$ is an ortho-substituted- or meta monosubstituted phenyl group; provided that $R_9$ and $R_{10}$ are free of amines and sulfur compounds.

There is also provided a display and an area lighting device incorporating the OLED device. Devices of the invention exhibit a desired operational stability.

DETAILED DESCRIPTION OF THE INVENTION

Figure 1:
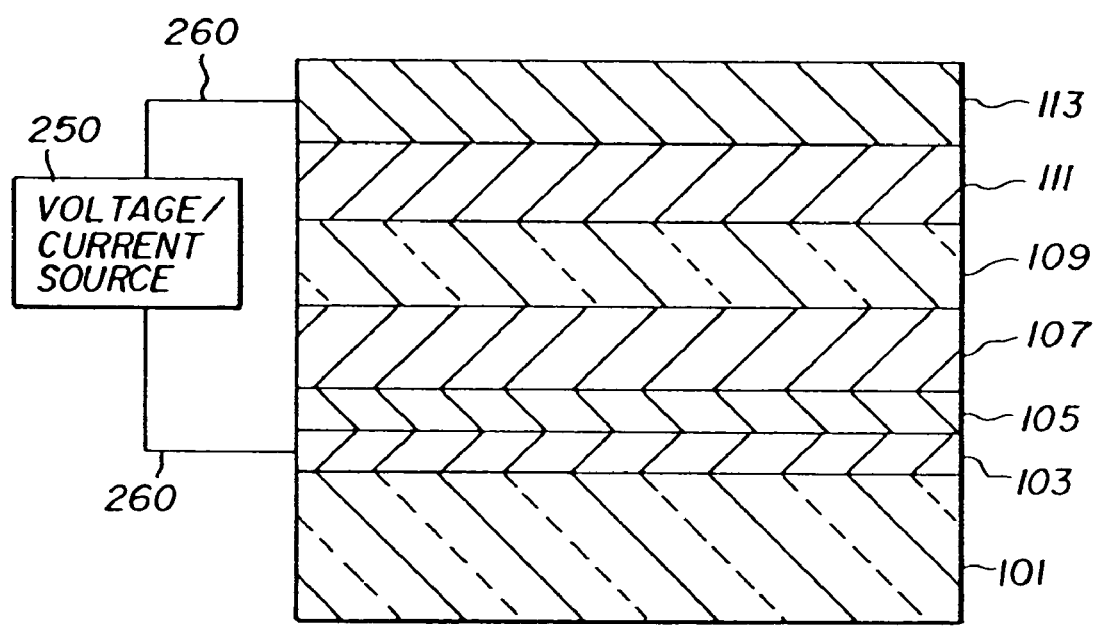
FIG. 1 shows a cross-section of a typical OLED device in which this invention may be used.

The invention is generally summarized above. Particular examples of hosts are defined in Formula (I)

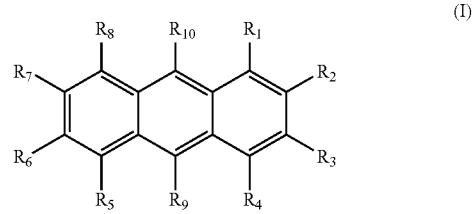

$R_1$–$R_8$ are H; $R_9$ is a biphenyl group containing no fused rings with aliphatic carbon ring members; provided that $R_9$ and $R_{10}$ are not the same, and are free of amines and sulfur compounds. Suitably, $R_9$ is a substituted biphenyl group such that it forms a fused aromatic ring system, including but not limited to a phenanthryl, perylene, or substituted with one or more substituents such as fluorine, cyano group, hydroxy, alkyl, trifluoromethyl, alkoxy, aryloxy, aryl, a heterotercyclic oxy group, carboxy, trimethylsilyl group, or an unsubstituted biphenyl group. Conveniently, $R_9$ is a 4-biphenyl (Inv-4, Inv-11), a phenanthryl comprising a 4-biphenyl (Inv-16), a cyano substituted 4-biphenyl (Inv-22). $R_{10}$ is an ortho-substituted or meta-monosubstituted phenyl group.

Suitably, $R_{10}$ is a phenyl group (a) ortho mono or bis-substituted with alkyl, trifluoromethyl, fluorine, cyano group, hydroxy, alkoxy, aryloxy, aryl including but not limited to phenyl, biphenyl, naphthyl, phenanthryl, fluoranthyl, terphenyl, or (b) mono meta-substituted with alkyl, trifluoromethyl, fluorine, cyano, hydroxy, alkoxy, aryloxy, aryl including but not limited to phenyl, biphenyl, naphthyl, terphenyl, phenanthryl, fluoranthyl, pyrenyl, a heterotercyclic oxy group. Conveniently, $R_{10}$ is a phenyl ring meta-substituted with a naphthyl (Inv-3, Inv-4), biphenyl, trifluoromethyl (Inv-6), or a trimethylsilyl (Inv-7) or ortho-substituted with a phenyl ring (Inv-1, Inv-4).

Unless otherwise specifically stated, use of the term "substituted" or "substituent" means any group or atom other than hydrogen. Unless otherwise specifically stated, use of the term "aromatic ring system" means a system of one ring or more than one ring fused together, where the entire ring system is aromatic. Unless otherwise specifically stated, use of the term "substituted phenyl ring" means a phenyl ring that is substituted and may be substituted to form one substituted or unsubstituted fused aromatic ring system, or more than one substituted or unsubstituted fused aromatic ring systems. Unless otherwise provided, when a group (including a compound or complex) containing a substitutable hydrogen is referred to, it is also intended to encompass not only the unsubstituted form, but also form further substituted with any substituent group or groups as herein mentioned, including a fused ring, so long as the substituent does not destroy properties necessary for utility. Suitably, a substituent group may be halogen or may be bonded to the remainder of the molecule by an atom of carbon, silicon, oxygen, or phosphorous.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups. The host of the invention is preferably used in combination with a dopant to yield a maximum emission in a device between 430–470 nm.

It has been found that unsymmetric anthracenes are extremely useful in OLED devices that exhibit high efficiencies. These compounds are useful in OLED devices that produce white light as well as in full color OLED devices and motion imaging devices.

Useful compounds of this invention include:

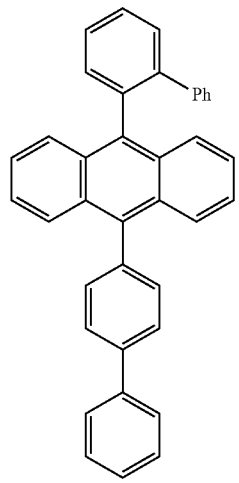

Inv-1

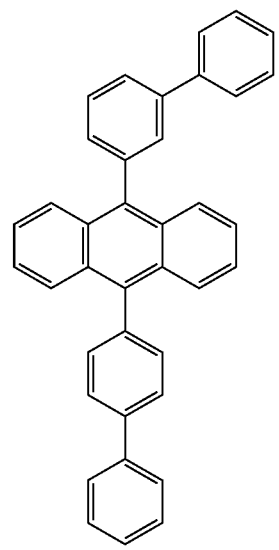

Inv-2

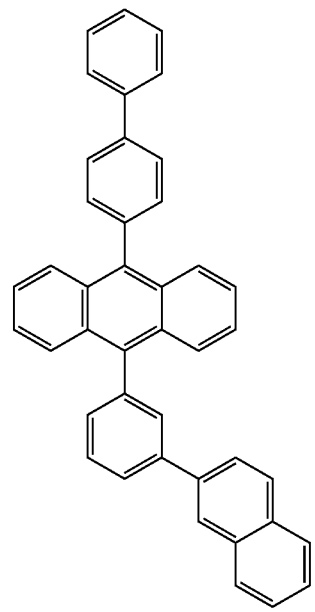

Inv-3

Inv-4
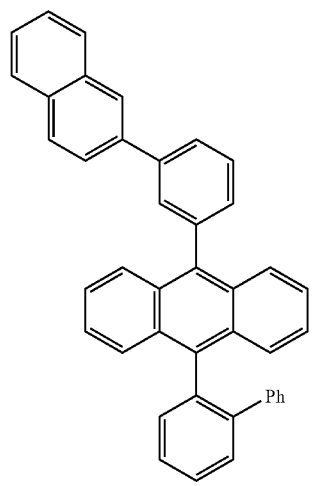
Inv-5
Inv-6
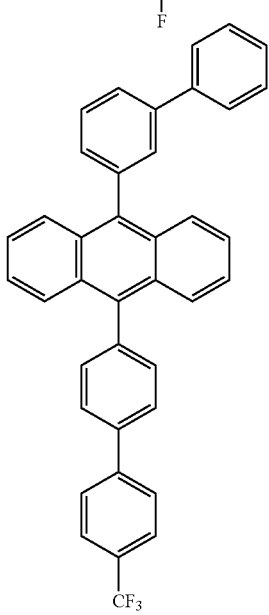
Inv-7
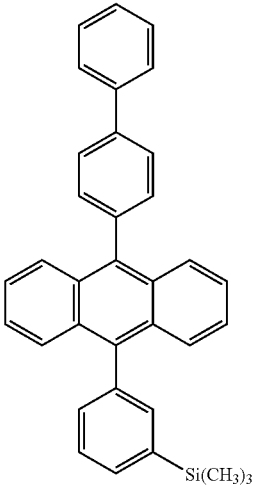
Inv-8
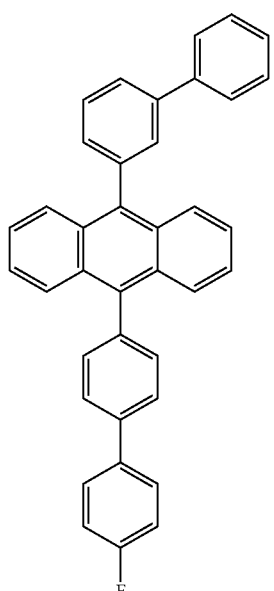
Inv-9

-continued
Inv-10
Inv-11
Inv-12
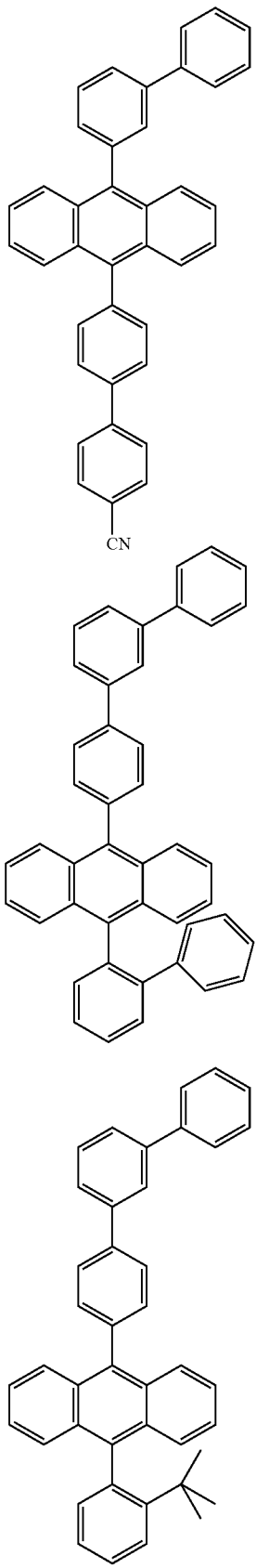
-continued
Inv-13
Inv-14
Inv-15
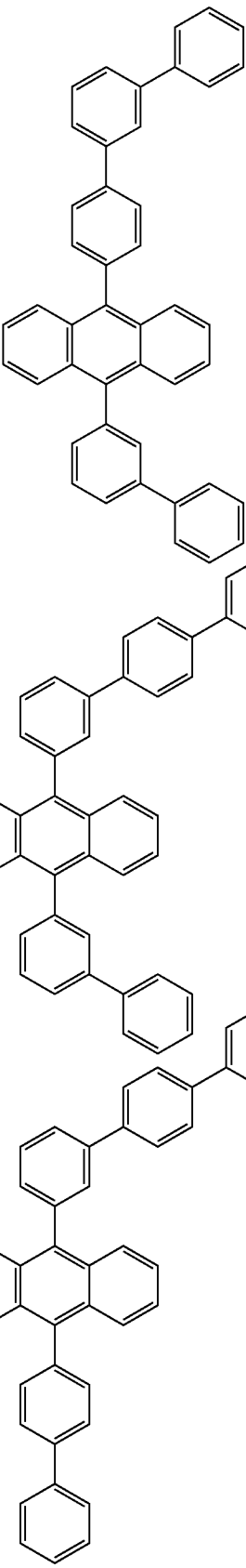

Inv-16
Inv-17
Inv-18

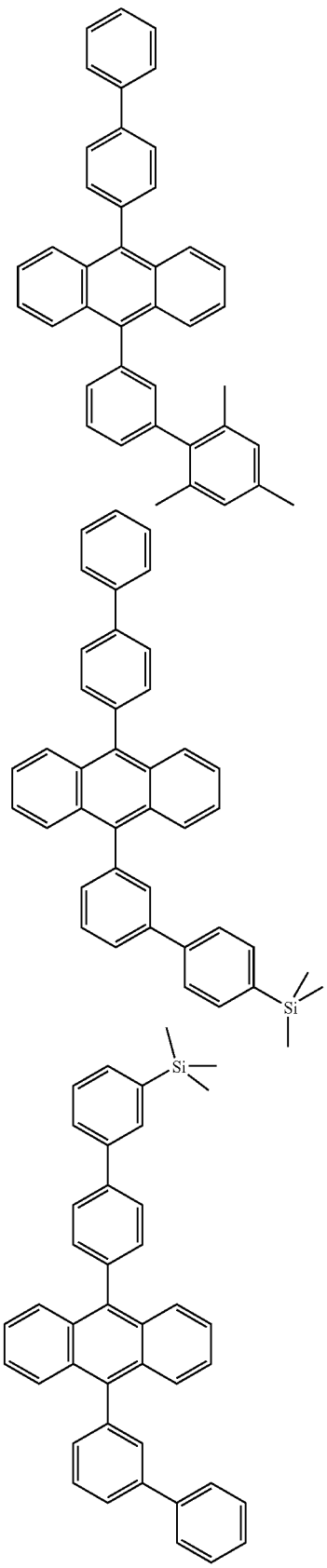

Compounds of the invention are typically employed in a light emitting layer comprising a certain thickness, together with a dopant as defined below. Examples of useful emitting materials include derivatives of anthracene, fluorene derivatives, periflanthene derivatives, indenoperylene derivatives, bis(azinyl)amine boron compounds. Suitably, the dopant comprises a quinacridone such as L7, or a perylene such as L2, a coumarin such as L30, bis(azinyl)methane or amine boron complexes such as L50, L51 and L52, aminostyryl derivatives such as L47. Conveniently, the dopants comprise a blue or blue-green dopant such as L2 and L50, and L47, or a green dopant such as the quinacridone L7.

The host of the invention is useful in a white device architecture, in a combination with a blue-green dopant.

The host of the invention can be used in combination with other blue or green co-host to improve the stability of a certain application. The co-host can be a small molecule or a polymeric material. Useful co-hosts include but are not limited to polyfluorenes, polyvinylarylenes, metal complexes of 8-hydroxyquinoline, benzazole derivatives, distyrylarylenes, carbazoles. Suitably the co-host is tris(8-quinolinolato)aluminum(III) (Alq).

It is an advantage of the hosts of the invention that they are free of sulfur and amines. The process of preparing the materials as well as their purification is simple and efficient and environmentally friendly, thus making these compounds conveniently manufacturable.

General Device Architecture

The present invention can be employed in most OLED device configurations. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers wherein the present invention can be successfully practiced. The essential requirements of an OLED are an anode, a cathode, and an organic light-emitting layer located between the anode and cathode. Additional layers may be employed as more fully described hereafter.

Anode

When the desired electroluminescent light emission (EL) is viewed through anode, the anode should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode. For applications where EL emission is viewed only through the cathode, the transmissive characteristics of the anode are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize shorts or enhance reflectivity.

Cathode

When light emission is viewed solely through the anode, the cathode used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising the cathode and a thin electron-injection layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. Other useful cathode material sets include, but are not limited to, those disclosed in U.S. Pat. Nos. 5,059,861; 5,059,862, and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. Nos. 4,885,211, 5,247,190, JP 3,234,963, U.S. Pat. Nos. 5,703,436, 5,608,287, 5,837,391, 5,677,572, 5,776,622, 5,776,623, 5,714,838, 5,969,474, 5,739,545, 5,981,306, 6,137,223, 6,140,763, 6,172,459, EP 1 076 368, U.S. Pat. Nos. 6,278,236, and 6,284,3936. Cathode materials are typically deposited by any suitable method such as evaporation, sputtering, or chemical vapor deposition. When needed, patterning can be achieved through many well known methods including, but not limited to, through-mask deposition, integral shadow masking as described in U.S. Pat. No. 5,276,380 and EP 0 732 868, laser ablation, and selective chemical vapor deposition.

Light-Emitting Layer (LEL)

This invention is primarily directed to the light-emitting layer (LEL). As more fully described in U.S. Pat. Nos. 4,769,292 and 5,935,721, the light-emitting layer (LEL) of the organic EL element includes a luminescent fluorescent or phosphorescent material where electroluminescence is produced as a result of electron-hole pair recombination in this region. The light-emitting layer can be comprised of a single material, but more commonly consists of a host material doped with a guest emitting material or materials where light emission comes primarily from the emitting materials and can be of any color. The host materials in the light-emitting layer can be an electron-transporting material, as defined below, a hole-transporting material, as defined above, or another material or combination of materials that support hole-electron recombination. The emitting material is usually chosen from highly fluorescent dyes and phosphorescent compounds, e.g., transition metal complexes as described in WO 98/55561, WO 00/18851, WO 00/57676, and WO 00/70655. Emitting materials are typically incorporated at 0.01 to 10% by weight of the host material.

The host and emitting materials can be small non-polymeric molecules or polymeric materials such as polyfluorenes and polyvinylarylenes (e.g., poly(p-phenylenevinylene), PPV). In the case of polymers, small molecule emitting materials can be molecularly dispersed into a polymeric host, or the emitting materials can be added by copolymerizing a minor constituent into a host polymer.

An important relationship for choosing an emitting material is a comparison of the bandgap potential which is defined as the energy difference between the highest occupied molecular orbital and the lowest unoccupied molecular orbital of the molecule. For efficient energy transfer from the host to the emitting material, a necessary condition is that the band gap of the dopant is smaller than that of the host material. For phosphorescent emitters it is also important that the host triplet energy level of the host be high enough to enable energy transfer from host to emitting material.

Host and emitting materials known to be of use include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721, and 6,020,078.

Metal complexes of 8-hydroxyquinoline and similar derivatives (Formula E) constitute one class of useful host compounds capable of supporting electroluminescence, and are particularly suitable for light emission of wavelengths longer than 500 nm, e.g., green, yellow, orange, and red.

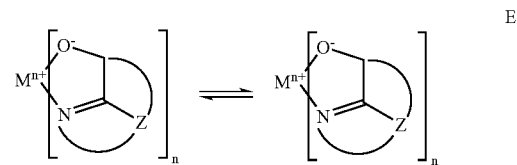

E wherein

M represents a metal;

n is an integer of from 1 to 4; and

Z independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

CO-1: Aluminum trisoxine [alias, tris(8-quinolinolato)aluminum(III)]

CO-2: Magnesium bisoxine [alias, bis(8-quinolinolato)magnesium(II)]

CO-3: Bis[benzo{f}-8-quinolinolato]zinc (II)

CO-4: Bis(2-methyl-8-quinolinolato)aluminum(III)-μ-oxo-bis(2-methyl-8-quinolinolato) aluminum(III)

CO-5: Indium trisoxine [alias, tris(8-quinolinolato)indium]

CO-6: Aluminum tris(5-methyloxine) [alias, tris(5-methyl-8-quinolinolato) aluminum(II)]
CO-7: Lithium oxine [alias, (8-quinolinolato)lithium(I)]
CO-8: Gallium oxine [alias, tris(8-quinolinolato)gallium (III)]
CO-9: Zirconium oxine [alias, tetra(8-quinolinolato)zirconium(IV)]

Derivatives of 9,10-di-(2-naphthyl)anthracene (Formula F) constitute one class of useful host materials capable of supporting electroluminescence, and are particularly suitable for light emission of wavelengths longer than 400 nm, e.g., blue, green, yellow, orange or red.

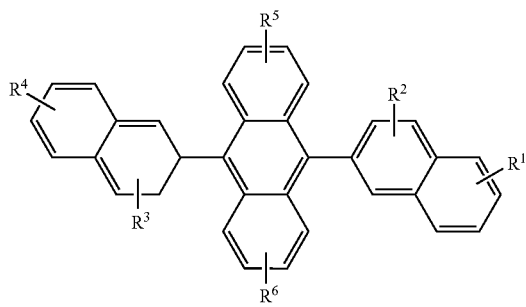

F wherein: $R^1$, $R^2$, $R^3$, $R^4$, $R^5$, and $R^6$ represent one or more substituents on each ring where each substituent is individually selected from the following groups:

Group 1: hydrogen, or alkyl of from 1 to 24 carbon atoms;
Group 2: aryl or substituted aryl of from 5 to 20 carbon atoms;
Group 3: carbon atoms from 4 to 24 necessary to complete a fused aromatic ring of anthracenyl; pyrenyl, or perylenyl;
Group 4: heteroaryl or substituted heteroaryl of from 5 to 24 carbon atoms as necessary to complete a fused heteroaromatic ring of furyl, thienyl, pyridyl, quinolinyl or other heterocyclic systems;
Group 5: alkoxylamino, alkylamino, or arylamino of from 1 to 24 carbon atoms; and
Group 6: fluorine, chlorine, bromine or cyano.

Illustrative examples include 9,10-di-(2-naphthyl)anthracene and 2-t-butyl-9, 10-di-(2-naphthyl)anthracene. Other anthracene derivatives can be useful as a host in the LEL, including derivatives of 9,10-bis[4-(2,2-diphenylethenyl)phenyl]anthracene.

Benzazole derivatives (Formula G) constitute another class of useful host materials capable of supporting electroluminescence, and are particularly suitable for light emission of wavelengths longer than 400 nm, e.g., blue, green, yellow, orange or red.

G

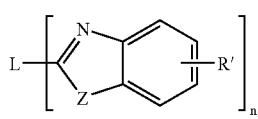

Where:
n is an integer of 3 to 8;
Z is O, NR or S; and

R and R' are individually hydrogen; alkyl of from 1 to 24 carbon atoms, for example, propyl, t-butyl, heptyl, and the like; aryl or hetero-atom substituted aryl of from 5 to 20 carbon atoms for example phenyl and naphthyl, furyl, thienyl, pyridyl, quinolinyl and other heterocyclic systems; or halo such as chloro, fluoro; or atoms necessary to complete a fused aromatic ring;

L is a linkage unit consisting of alkyl, aryl, substituted alkyl, or substituted aryl, which conjugately or unconjugately connects the multiple benzazoles together. An example of a useful benzazole is 2, 2', 2"-(1,3,5-phenylene) tris[1-phenyl-1H-benzimidazole].

Distyrylarylene derivatives are also useful hosts, as described in U.S. Pat. No. 5,121,029. Carbazole derivatives are particularly useful hosts for phosphorescent emitters.

Useful fluorescent emitting materials include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrilium and thiapyrilium compounds, fluorene derivatives, periflanthene derivatives, indenoperylene derivatives, bis(azinyl)amine boron compounds, bis(azinyl)methane compounds, and carbostyryl compounds. Illustrative examples of useful materials include, but are not limited to, the following:

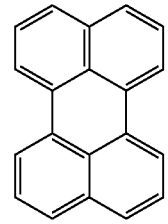

L1

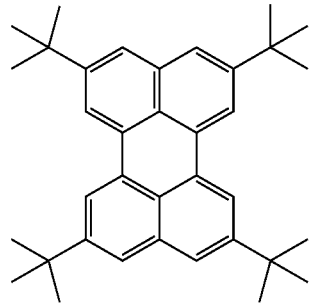

L2

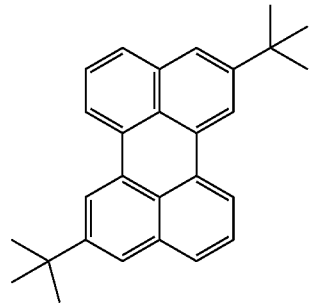

L3

-continued
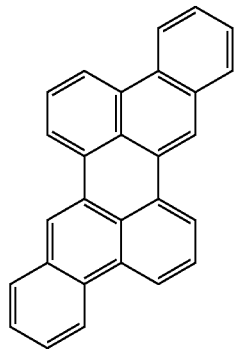
L4
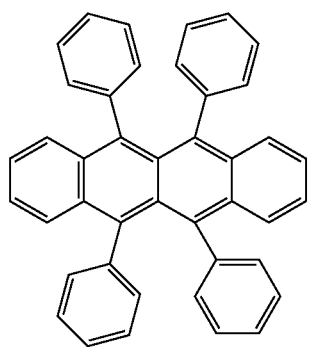
L5
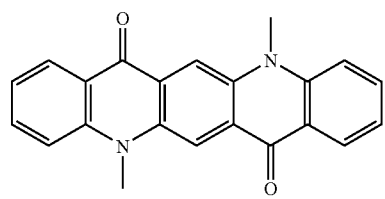
L6
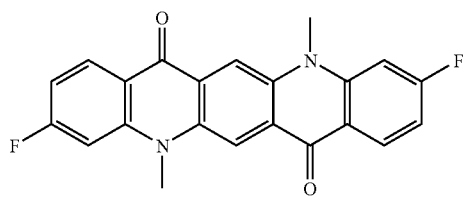
L7
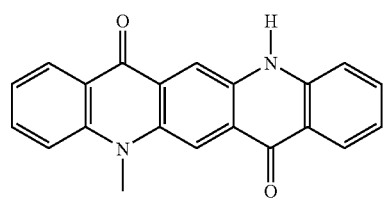
L8
-continued
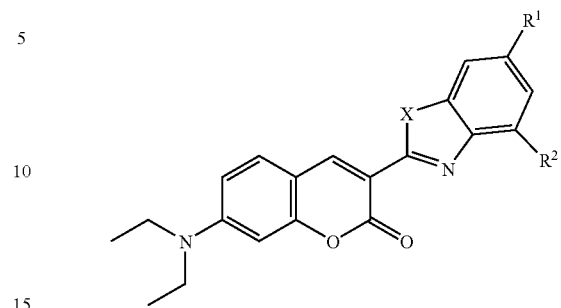
| | X | R1 | R2 |
|---|---|---|---|
| L9 | O | H | H |
| L10 | O | H | Methyl |
| L11 | O | Methyl | H |
| L12 | O | Methyl | Methyl |
| L13 | O | H | t-butyl |
| L14 | O | t-butyl | H |
| L15 | O | t-butyl | t-butyl |
| L16 | S | H | H |
| L17 | S | H | Methyl |
| L18 | S | Methyl | H |
| L19 | S | Methyl | H |
| L20 | S | H | t-butyl |
| L21 | S | t-butyl | H |
| L22 | S | t-butyl | t-butyl |
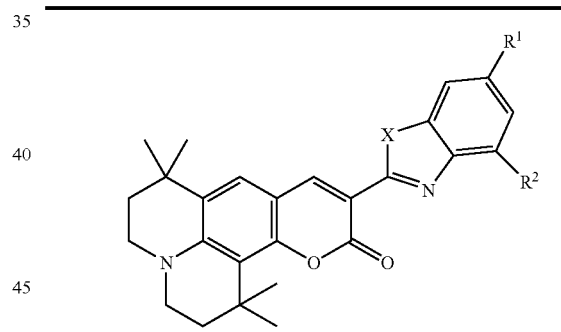
| | X | R1 | R2 |
|---|---|---|---|
| L23 | O | H | H |
| L24 | O | H | Methyl |
| L25 | O | Methyl | H |
| L26 | O | Methyl | Methyl |
| L27 | O | H | t-butyl |
| L28 | O | t-butyl | H |
| L29 | O | t-butyl | t-butyl |
| L30 | S | H | H |
| L31 | S | H | Methyl |
| L32 | S | Methyl | H |
| L33 | S | Methyl | Methyl |
| L34 | S | H | t-butyl |
| L35 | S | t-butyl | H |
| L36 | S | t-butyl | t-butyl |

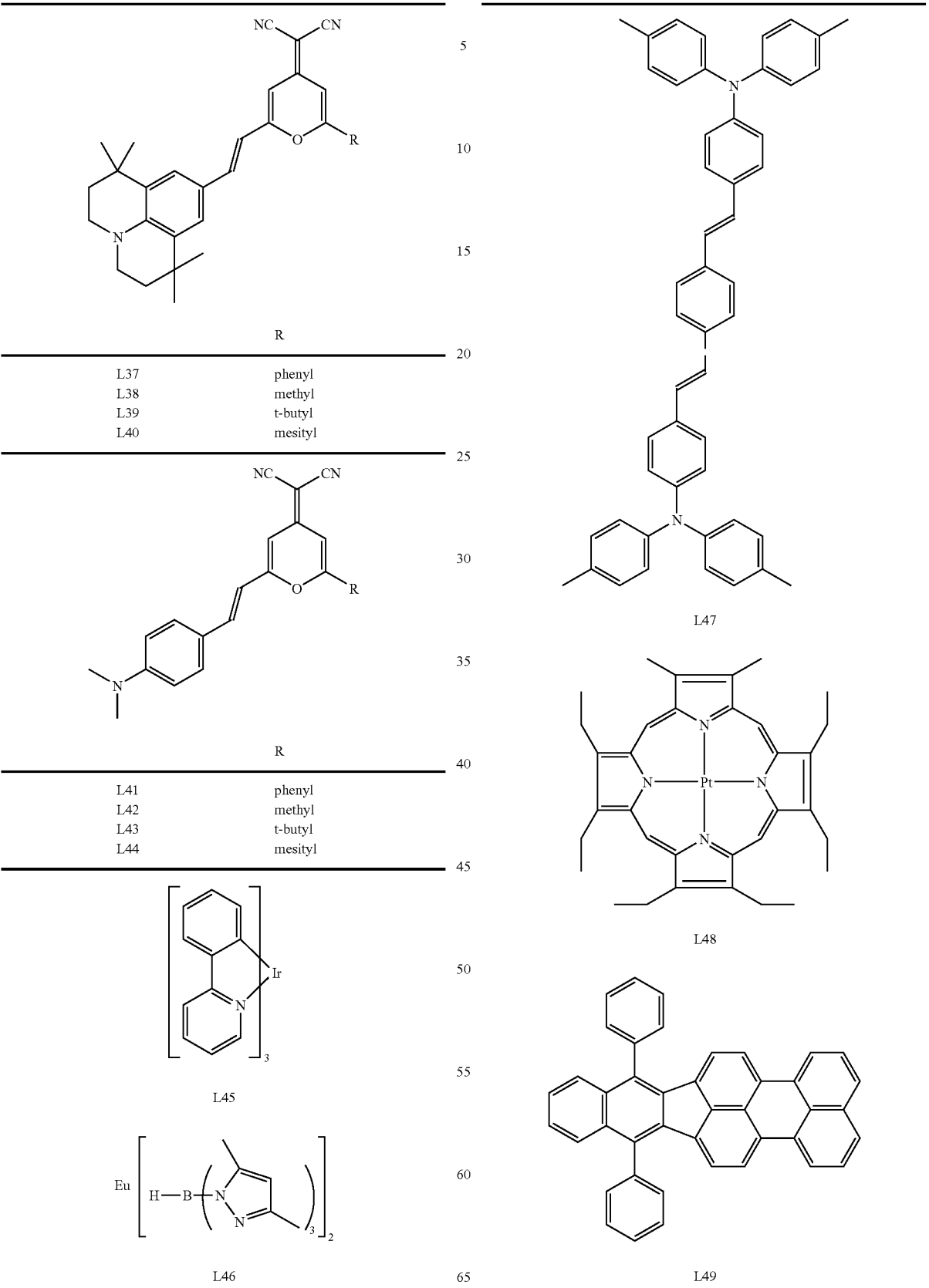
| | R |
|---|---|
| L37 | phenyl |
| L38 | methyl |
| L39 | t-butyl |
| L40 | mesityl |
| | R |
|---|---|
| L41 | phenyl |
| L42 | methyl |
| L43 | t-butyl |
| L44 | mesityl |
L45
L46
L47
L48
L49

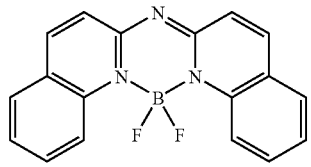

L50

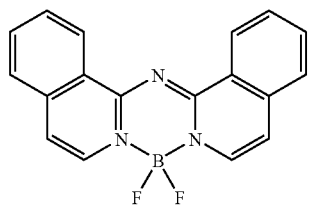

L51

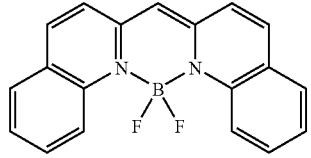

L52

Device

A typical structure, especially useful for of a small molecule device, is shown in FIG. 1 and is comprised of a substrate 101, an anode 103, a hole-injecting layer 105, a hole-transporting layer 107, a light-emitting layer 109, an electron-transporting layer 111, and a cathode 113. These layers are described in detail below. Note that the substrate may alternatively be located adjacent to the cathode, or the substrate may actually constitute the anode or cathode. The organic layers between the anode and cathode are conveniently referred to as the organic EL element. Also, the total combined thickness of the organic layers is preferably less than 500 nm.

The anode and cathode of the OLED are connected to a voltage/current source 250 through electrical conductors 260. The OLED is operated by applying a potential between the anode and cathode such that the anode is at a more positive potential than the cathode. Holes are injected into the organic EL element from the anode and electrons are injected into the organic EL element at the anode. Enhanced device stability can sometimes be achieved when the OLED is operated in an AC mode where, for some time period in the cycle, the potential bias is reversed and no current flows. An example of an AC driven OLED is described in U.S. Pat. No. 5,552,678.

Substrate

The OLED device of this invention is typically provided over a supporting substrate 101 where either the cathode or anode can be in contact with the substrate. The electrode in contact with the substrate is conveniently referred to as the bottom electrode. Conventionally, the bottom electrode is the anode, but this invention is not limited to that configuration. The substrate can either be light transmissive or opaque, depending on the intended direction of light emission. The light transmissive property is desirable for viewing the EL emission through the substrate. Transparent glass or plastic is commonly employed in such cases. The substrate may be a complex structure comprising multiple layers of materials. This is typically the case for active matrix substrates wherein TFTs are provided below the OLED layers. It is still necessary that the substrate, at least in the emissive pixilated areas, be comprised of largely transparent materials such as glass or polymers. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, silicon, ceramics, and circuit board materials. Again, the substrate may be a complex structure comprising multiple layers of materials such as found in active matrix TFT designs. Of course it is necessary to provide in these device configurations a light-transparent top electrode.

Hole-Injecting Layer (HIL)

While not always necessary, it is often useful that a hole-injecting layer 105 be provided between anode 103 and hole-transporting layer 107. The hole-injecting material can serve to improve the film formation property of subsequent organic layers and to facilitate injection of holes into the hole-transporting layer. Suitable materials for use in the hole-injecting layer include, but are not limited to, porphyrinic compounds as described in U.S. Pat. No. 4,720,432, plasma-deposited fluorocarbon polymers as described in U.S. Pat. No. 6,208,075, and some aromatic amines, for example, m-MTDATA (4,4',4"-tris[(3-methylphenyl)phenylamino]triphenylamine). Alternative hole-injecting materials reportedly useful in organic EL devices are described in EP 0 891 121 A1 and EP 1 029 909 A1.

Hole-Transporting Layer (HTL)

The hole-transporting layer 107 of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al U.S. Pat. Nos. 3,567,450 and 3,658,520.

A more preferred class of aromatic tertiary amines are those which include at least two aromatic tertiary amine moieties as described in U.S. Pat. Nos. 4,720,432 and 5,061,569. Such compounds include those represented by structural formula (A).

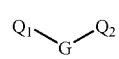

A wherein $Q_1$ and $Q_2$ are independently selected aromatic tertiary amine moieties and G is a linking group such as an arylene, cycloalkylene, or alkylene group of a carbon to carbon bond. In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural formula (A) and containing two triarylamine moieties is represented by structural formula (B):

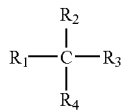

where
R₁ and R₂ each independently represents a hydrogen atom, an aryl group, or an alkyl group or R₁ and R₂ together represent the atoms completing a cycloalkyl group; and R₃ and R₄ each independently represents an aryl group, which is in turn substituted with a diaryl substituted amino group, as indicated by structural formula (C):

wherein $R_5$ and $R_6$ are independently selected aryl groups. In one embodiment, at least one of $R_5$ or $R_6$ contains a polycyclic fused ring structure, e.g., a naphthalene.

Another class of aromatic tertiary amines are the tetraaryldiamines. Desirable tetraaryldiamines include two diarylamino groups, such as indicated by formula (C), linked through an arylene group. Useful tetraaryldiamines include those represented by formula (D).

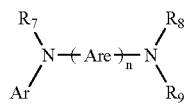

wherein each Are is an independently selected arylene group, such as a phenylene or anthracene moiety, n is an integer of from 1 to 4, and Ar, R₇, R₈, and R₉ are independently selected aryl groups.

In a typical embodiment, at least one of Ar, R₇, R₈, and R₉ is a polycyclic fused ring structure, e.g., a naphthalene.

The various alkyl, alkylene, aryl, and arylene moieties of the foregoing structural formulae (A), (B), (C), (D), can each in turn be substituted.

Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms—e.g., cyclopentyl, cyclohexyl, and cycloheptyl ring structures. The aryl and arylene moieties are usually phenyl and phenylene moieties.

The hole-transporting layer can be formed of a single or a mixture of aromatic tertiary amine compounds. Specifically, one may employ a triarylamine, such as a triarylamine satisfying the formula (B), in combination with a tetraaryldiamine, such as indicated by formula (D). When a triarylamine is employed in combination with a tetraaryldiamine, the latter is positioned as a layer interposed between the triarylamine and the electron injecting and transporting layer. Illustrative of useful aromatic tertiary amines are the following:

1,1-Bis(4-di-p-tolylaminophenyl)cyclohexane
1,1-Bis(4-di-p-tolylaminophenyl)-4-phenylcyclohexane
4,4'-Bis(diphenylamino)quadriphenyl
Bis(4-dimethylamino-2-methylphenyl)-phenylmethane
N,N,N-Tri(p-tolyl)amine
4-(di-p-tolylamino)-4'-[4(di-p-tolylamino)-styryl]stilbene
N,N,N',N'-Tetra-p-tolyl-4-4'-diaminobiphenyl
N,N,N',N'-Tetraphenyl-4,4'-diaminobiphenyl
N,N,N',N'-tetra-1-naphthyl-4,4'-diaminobiphenyl
N,N,N',N'-tetra-2-naphthyl-4,4'-diaminobiphenyl
N-Phenylcarbazole
4,4'-Bis[N-(1-naphthyl)-N-phenylamino]biphenyl
4,4'-Bis[N-(1-naphthyl)-N-(2-naphthyl)amino]biphenyl
4,4"-Bis[N-(1-naphthyl)-N-phenylamino]$_p$-terphenyl
4,4'-Bis[N-(2-naphthyl)-N-phenylamino]biphenyl
4,4'-Bis[N-(3-acenaphthenyl)-N-phenylamino]biphenyl
1,5-Bis[N-(1-naphthyl)-N-phenylamino]naphthalene
4,4'-Bis[N-(9-anthryl)-N-phenylamino]biphenyl
4,4"-Bis[N-(1-anthryl)-N-phenylamino]-p-terphenyl
4,4'-Bis[N-(2-phenanthryl)-N-phenylamino]biphenyl
4,4'-Bis[N-(8-fluoranthenyl)-N-phenylamino]biphenyl
4,4'-Bis[N-(2-pyrenyl)-N-phenylamino]biphenyl
4,4'-Bis[N-(2-naphthacenyl)-N-phenylamino]biphenyl
4,4'-Bis[N-(2-perylenyl)-N-phenylamino]biphenyl
4,4'-Bis[N-(1-coronenyl)-N-phenylamino]biphenyl
2,6-Bis(di-p-tolylamino)naphthalene
2,6-Bis[di-(1-naphthyl)amino]naphthalene
2,6-Bis[N-(1-naphthyl)-N-(2-naphthyl)amino]naphthalene
N,N,N',N'-Tetra(2-naphthyl)-4,4"-diamino-p-terphenyl
4,4'-Bis {N-phenyl-N-[4-(1-naphthyl)-phenyl]amino}biphenyl
4,4'-Bis[N-phenyl-N-(2-pyrenyl)amino]biphenyl
2,6-Bis[N,N-di(2-naphthyl)amine]fluorene
1,5-Bis[N-(1-naphthyl)-N-phenylamino]naphthalene
4,4',4"-tris[(3-methylphenyl)phenylamino]triphenylamine Another class of useful hole-transporting materials includes polycyclic aromatic compounds as described in EP 1 009 041. Tertiary aromatic amines with more than two amine groups may be used including oligomeric materials. In addition, polymeric hole-transporting materials can be used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

Electron-Transporting Layer (ETL)

Preferred thin film-forming materials for use in forming the electron-transporting layer 111 of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those satisfying structural formula (E), previously described.

Other electron-transporting materials include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials. Triazines are also known to be useful as electron transporting materials.

Other Useful Organic Layers and Device Architecture

In some instances, layers 109 and 111 can optionally be collapsed into a single layer that serves the function of supporting both light emission and electron transportation. It also known in the art that emitting materials may be included in the hole-transporting layer, which may serve as a host. Multiple materials may be added to one or more layers in order to create a white-emitting OLED, for example, by combining blue- and yellow-emitting materials, cyan- and red-emitting materials, or red-, green-, and blue-emitting materials. White-emitting devices are described, for example, in EP 1 187 235, US 20020025419, EP 1 182 244, U.S. Pat. Nos. 5,683,823, 5,503,910, 5,405,709, and 5,283,182 and may be equipped with a suitable filter arrangement to produce a color emission.

Additional layers such as electron or hole-blocking layers as taught in the art may be employed in devices of this invention. Hole-blocking layers are commonly used to improve efficiency of phosphorescent emitter devices, for example, as in US 20020015859.

This invention may be used in so-called stacked device architecture, for example, as taught in U.S. Pat. Nos. 5,703,436 and 6,337,492.

Deposition of Organic Layers

The organic materials are conveniently deposited through sublimation, but can be deposited by other means such as from a solvent with an optional binder to improve film formation. If the material is a polymer, solvent deposition is usually preferred. The material to be deposited by sublimation can be vaporized from a sublimator "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimator boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. Nos. 5,688,551, 5,851,709 and 6,066,357) and inkjet method (U.S. Pat. No. 6,066,357).

Encapsulation

Most OLED devices are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiOx, Teflon, and alternating inorganic/polymeric layers are known in the art for encapsulation.

Optical Optimization

OLED devices of this invention can employ various well-known optical effects in order to enhance its properties if desired. This includes optimizing layer thicknesses to yield maximum light transmission, providing dielectric mirror structures, replacing reflective electrodes with light-absorbing electrodes, providing anti glare or anti-reflection coatings over the display, providing a polarizing medium over the display, or providing colored, neutral density, or color conversion filters over the display. Filters, polarizers, and anti-glare or anti-reflection coatings may be specifically provided over the cover or as part of the cover.

The entire contents of the patents and other publications referred to in this specification are incorporated herein by reference.

EXAMPLES

The invention and its advantages are further illustrated by the specific examples that follow. The embodiments of the invention may also exhibit thermal stability.

EXAMPLE 1

Preparation of Inv-1 a) Preparation of 9-(4-biphenyl)anthracene. 9-Bromoanthracene (19.5 g, 75.8 mmol, 1 eq) and (1,1'-biphenyl-4-yl) boronic acid (15.0 g, 75.8 mmol, 1 eq) were combined in 100 ml of toluene and the resulting mixture degassed by sonication for about 15 min. tetrakis(triphenylphosphine) palladium (0.650 g, 0.568 mmol, 0.75%) was added and the resulting mixture was thoroughly stirred under nitrogen while 150 ml of 2M $Na_2CO_3$ were added and the mixture heated to reflux via heating mantle. The reaction was left to reflux overnight, during which time the product had precipitated out. The solid isolated by filtration and the organic phase was washed with water until the washings were neutral. The solid isolated was dissolved in hot toluene and filtered through glass fiber filter paper to remove palladium salts. The toluene phases were combined and concentrated to about 100 mL residue, which was left to recrystallize overnight. The product recrystallized was isolated by filtration, and because the mother liquor contained a substantial amount of product, a second crop was obtained. The two crops had similar purities by TLC and were combined to yield a total of 2.0 g of product (84%).

b) Preparation of 9-bromo, 10-(4-biphenyl)anthracene. 9-(4-biphenyl)anthracene (18 g, 54.5 mmol, 1 eq) and N-bromosuccinimide (10.2 g, 57.2 mmol, 1.05 eq) were combined with 140 ml $CH_2Cl_2$ in a 500 ml round bottom flask. The thick mixture was stirred at room temperature for 15 minutes with a 100 W shining on it to initiate the reaction. Because the reaction mixture appeared to have thickened, about 80 mL more of $CH_2Cl_2$ were added to the reaction mixture. At no time the mixture has cleared. TLC (P950: $CH_2Cl_2$/9:1) indicated complete reaction after 20 minutes. The heterogeneous mixture was refrigerated overnight and the solid product isolated by filtration, to yield 17.2 g of clean product. The filtrate was concentrated and chilled to yield a second crop of solid, similar in purity to the first isolated material. The combined crops yielded 97% (21.5 g) of pure product.

c) Preparation of 9-(4-biphenyl), 10-(2-biphenyl)anthracenes. 9-Bromo, 10-(4-biphenyl)anthracene (3.0 g, 7.33 mmol, 1 eq), 2-biphenylboronic acid (1.52 g, 7.70 mmol, 1.05 eq) together with $(PPh_3)_2PdCl_2$ (0.16 g, 0.7 eq %) were combined in 50 mL toluene in a 250 mL round bottom flask, and the resulting suspension was sonicated for 30 min under $N_2$. A 2M solution of $Na_2CO_3$ was added and the resulting heterogeneous mixture was quickly brought to reflux. The mixture was left at reflux overnight time during which the mixture stayed light yellow indicative of the catalyst still being active. The mixture was filtered hot, through a glass fiber filter paper to remove palladium salts. The organic phase was isolated and washed with water until washings were neutral. The Original aqueous phase was saturated with brine and extracted with methylene chloride. The organic layers were combined, and the solution concentrated to about 40 mL and left standing in the fridge. No solid was precipitating out, so 10 mL of heptane were added and the solution placed in the fridge. After 2 h, a greenish solid crystallized (2.7 g). The mother liquor was concentrated and more heptane was added to yield another crop of crystalline solid, identical in purity to the first. The total weight of combined product was 3.2 g (90%). The product was sublimed (200–210° C.) prior to device fabrication.

d)

EXAMPLES 2, 3

Inventive EL Devices

An EL device satisfying the requirements of the invention was constructed in the following manner:

A glass substrate coated with a 42 nm layer of indium-tin oxide (ITO) as the anode was sequentially ultrasonicated in a commercial detergent, rinsed in deionized water, degreased in toluene vapor and exposed to oxygen plasma for about 1 min.
  a) Over the ITO was deposited a 1 nm fluorocarbon hole-injecting layer (CFx) by plasma-assisted deposition of $CHF_3$.
  b) A hole-transporting layer of N,N'-di-1-naphthalenyl-N, N'-diphenyl-4, 4'-diaminobiphenyl (NPB) having a thickness of 75 nm was then evaporated from a tantalum boat.
  c) A 20–40 nm light-emitting layer of Inyl doped with various amounts of dopant depending upon the dopant used, was then deposited onto the hole-transporting layer. These materials were co-evaporated from tantalum boats. Herein, doping percentage is reported based on volume/volume ratio. The specific dopant, percentage and host thickness are indicated in Table1.
  d) A 30 nm electron-transporting layer of tris(8-quinolinolato)aluminum (III) (Alq) was then deposited onto the light-emitting layer. This material was also evaporated from a tantalum boat.
  e) On top of the Alq layer was deposited a 220 nm cathode formed of a 10:1 volume ratio of Mg and Ag.

The above sequence completed the deposition of the EL device. The device was then hermetically packaged in a dry glove box for protection against ambient environment.

EXAMPLES 4, 5, 6, 7, 8

Comparative EL Devices

EL devices of comparative examples were fabricated in the same manner as Example 2 except that, in place of Inv-1, other anthracene derivatives not part of this invention, were used as hosts.

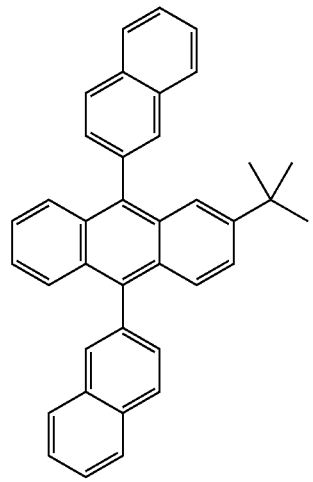

Comp-1

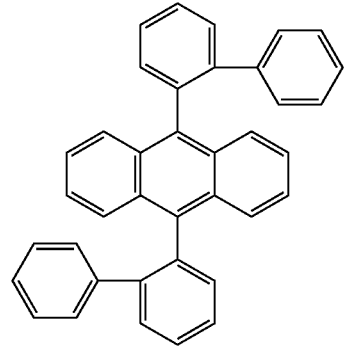

Comp-2

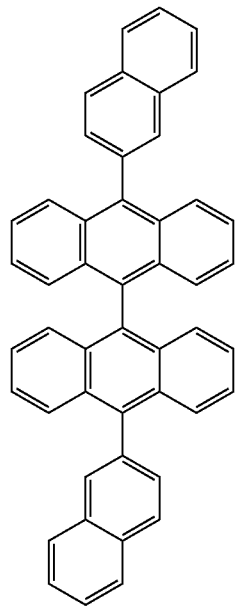

Comp-3

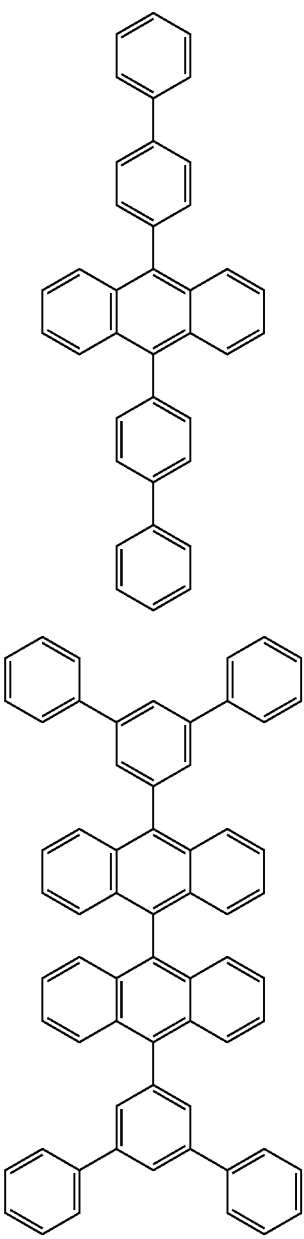

Comp-4

Comp-5

The cells thus formed in Examples 2–8 were tested for efficiency in the form of luminance yield (cd/A) measured at 20 mA/cm$^2$. CIE color x and y coordinates were determined. It is desirable to have a luminance yield of at least about 2.2 cd/A and preferably greater than about 3 cd/A, for a blue device. The luminance loss was measured by subjecting the cells to a constant current density of 20 mA/cm$^2$ at 70° C., or at 40 mA/cm$^2$ at RT (room temperature), to various amounts of time that are specified for each individual cell/example. The extrapolated values are estimated based on real data at 20 mA/cm$^2$ and 70° C., or at 40 mA/cm$^2$ and RT. Useful stability for use in a display device is desirably less than about 40% loss after about 300 hours of these accelerated aging conditions. All of these testing data are shown in Table 1b and Table 2b.

TABLE 1a

Device architecture for Examples 2–4

| Type | Dopant % | Layer Thickness |
|---|---|---|
| Example2, Inv-1 | L2, 2% | 200 A |
| Example3, Inv-1 | L2, 2% | 400 A |
| Example4, Comp-1 | L2, 1% | 200 A |

TABLE 1b

Improved stability of Inv-1 relative to the reference Comp-1 (Examples 2–4)

| Type | Efficiency (W/A) | Yield (cd/A) | CIEx | CIEy | Luminance Loss % (h) | T50 extrapolated |
|---|---|---|---|---|---|---|
| Example2 Inv-1 | 0.042 | 2.55 | 0.149 | 0.209 | 35 (600 h) | 960 h |
| Example3 Inv-1 | 0.040 | 2.68 | 0.150 | 0.247 | 40 (600 h) | 900 h |
| Example4 Comp-1 | 0.044 | 2.31 | 0.145 | 0.172 | 43 (600 h) | 670 h |

Table 1b: Improved stability of Inv-1 relative to the reference Comp-1 (Examples 2–4)

Compound Inv-1 provides an advantage in stability over the check Comp-1. The devices in Table 1b were faded at 70° C. and 20 mA/cm$^2$, a more accelerated testing method.

TABLE 2a

Device architecture for Examples 5–8

| Type | Dopant % | Layer Thickness |
|---|---|---|
| Example5, Comp-2 | L2 1% | 200 A |
| Example6, Comp-3 | L2 2% | 200 A |
| Example7, Comp-4 | L2 1% | 200 A |
| Example8, Comp-5 | L2 2% | 200 A |

TABLE 2b

Comparative examples of symmetrical analogs (Examples 5–8)

| Type | Efficiency (W/A) | Yield (cd/A) | CIEx | CIEy | Luminance Loss % (h) | T50 extrapolated |
|---|---|---|---|---|---|---|
| Example5 Comp-2 | 0.046 | 2.80 | 0.151 | 0.210 | 37 (250 h), 70 C, 20 mA | 51 h |
| Example6 Comp-3 | 0.037 | 2.80 | 0.191 | 0.270 | 60 (220 h), RT, 20 mA | 80 h (real data) |
| Example7 Comp-4 | 0.005 | 0.63 | 0.281 | 0.461 | * | |
| Example8 Comp-5 | 0.043 | 2.76 | 0.163 | 0.224 | 35 (310 h), RT, 20 mA | 670 h |

* Example 7 illustrates the failure of Comp-4 in a device.

Operational stability could not be measured, as the device degrades within 1 minute under 9V battery. The material was vapor deposited and a device fabricated twice to yield the same results. It is thought that the high crystallinity of the solid in the bulk state renders al very low propensity for glass forming in a device. The fact that the device is very grainy in appearance may support the same hypothesis.

The data from examples 2–8 shows the significant improvement in stability of unsymmetrical monoanthracenes with L2. Comparing the data in Table 1b and Table 2b, there is a clear correlation between structural attributes (symmetry/unsymmetry) and performance in a device.

The invention has been described in detail with particular reference to certain preferred embodiments thereof, but it will be understood that variations and modifications can be effected within the spirit and scope of the invention.

PARTS LIST

101 Substrate
103 Anode
105 Hole-Injecting layer (HIL)
107 Hole-Transporting layer (HTL)
109 Light-Emitting layer (LEL)
111 Electron-Transporting layer (ETL)
113 Cathode
250 Current/Voltage source
260 Electrical conductors

What is claimed is:

1. An OLED device comprising an anode and a cathode and located there-between a light emitting layer containing a light emitting dopant and a host comprising a monoanthracene derivative of formula (I):

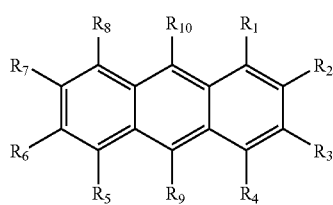
(I)

wherein
$R_1$–$R_8$ are H;
$R_9$ is not the same as $R_{10}$;
$R_9$ is a biphenyl group containing no fused rings with aliphatic carbon ring members;
$R_{10}$ is an ortho-substituted- or meta monosubstituted phenyl group wherein the substituent is selected from fluorine, hydroxy, cyano, alkyl, alkoxy, aryloxy, aryl, carboxy, trimethylsilyl, and heterocyclic oxy groups; provided that $R_9$ and $R_{10}$ are free of amines and sulfur compounds.

2. The device of claim 1 wherein $R_9$ is an unsubstituted biphenyl group.

3. The device of claim 1 wherein at least one of the phenyl rings of the biphenyl has a ring fused thereto.

4. The device of claim 1 wherein the biphenyl contains two phenyl ring groups without fused rings.

5. The device of claim 3 wherein the biphenyl is a 2-biphenyl.

6. The device of claim 3 wherein the biphenyl is a 3-biphenyl.

7. The device of claim 3 wherein the biphenyl is a 4-biphenyl.

8. The device of claim 1 wherein all of the phenyl rings of the biphenyl group are unsubstituted.

9. The device of claim 1 wherein the biphenyl is substituted with at least one substituent selected from fluorine, hydroxy, cyano, alkyl, alkoxy, aryloxy, aryl, carboxy, trimethylsilyl and heterocyclic oxy groups.

10. The device of claim 1 wherein $R_{10}$ is ortho-substituted.

11. The device of claim 10 wherein the ortho substituent is selected from fluorine, alkyl, and aryl groups.

12. The device of claim 10 wherein the $R_{10}$ ortho substituent is a phenyl group.

13. The device of claim 1 wherein $R_{10}$ is meta monosubstituted.

14. The device of claim 13 wherein the $R_{10}$ substituent is selected from fluorine, alkyl, and aryl groups.

15. The device of claim 13 where in the $R_{10}$ meta substituent is a phenyl group.

16. The device of claim 13 where in the meta substituent is a naphthyl group.

17. The device of claim 13 wherein the mete substituent is a biphenyl group.

18. The device of claim 1 wherein the light emitting dopant emits blue light.

19. The device of claim 1 wherein the light emitting dopant emits green light.

20. The device of claim 1 including in one or more light emitting layers compounds sufficient for the device to emit white light.

21. The device of claim 1 including a co-host.

22. The device of claim 21 including a polymeric co-host.

23. The device of claim 21 including an oxinoid compound co-host.

24. The device of claim 23 wherein the oxinoid is Alq.

25. A display incorporating the device of claim 1.

26. An area lighting system incorporating the device of claim 1.

* * * * *